(12) United States Patent
Chang

(10) Patent No.: US 11,377,686 B2
(45) Date of Patent: Jul. 5, 2022

(54) DNA SEQUENCING VIA DIRECT ELECTRICAL DETECTION WITH FREE SINGLE NUCLEOTIDE PAIRING WITH POLYMERASE

(71) Applicant: Seagate Technology LLC, Fremont, CA (US)

(72) Inventor: Thomas Young Chang, Menlo Park, CA (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 78 days.

(21) Appl. No.: 16/935,111

(22) Filed: Jul. 21, 2020

(65) Prior Publication Data

US 2021/0054447 A1    Feb. 25, 2021

Related U.S. Application Data

(60) Provisional application No. 62/889,331, filed on Aug. 20, 2019.

(51) Int. Cl.
*C12Q 1/6869* (2018.01)
*G01N 33/487* (2006.01)

(52) U.S. Cl.
CPC ..... *C12Q 1/6869* (2013.01); *G01N 33/48721* (2013.01); *C12Q 2600/156* (2013.01)

(58) Field of Classification Search
CPC ............ C12Q 1/6869; C12Q 2600/156; G01N 33/48721; B01L 2200/10; B01L 2300/0645; B01L 3/502761
See application file for complete search history.

(56) References Cited

U.S. PATENT DOCUMENTS

| | | | |
|---|---|---|---|
| 6,770,472 B2 | 8/2004 | Manalis et al. | |
| 7,785,785 B2 | 8/2010 | Pourmand et al. | |
| 8,313,907 B2 | 11/2012 | Pourmand et al. | |
| 2011/0281739 A1* | 11/2011 | Pourmand | G01N 27/3276 435/6.1 |

OTHER PUBLICATIONS

Chen et al ., Nature Nanotechnology, vol. 8, 452-563, Jun. 2013.*
Pourmand, Nader, et al., "Direct electrical detection of DNA synthesis," PNAS, vol. 103, No. 17; Apr. 25, 2006.

* cited by examiner

*Primary Examiner* — Cynthia B Wilder
(74) *Attorney, Agent, or Firm* — Holzer Patel Drennan

(57) ABSTRACT

A DNA sequencing device having a first conductor electrically insulated from a second conductor, a voltage source and an amplifier electrically connected in series with the first conductor and the second conductor, a DNA polymerase attached to the first conductor and to the second conductor with matching biotinylated tag molecules, and an electric current monitor. A non-discriminating electrical signal is provided by the polymerase during pairing, which signal can be used as a marker to indicate that transcription is occurring between a single-type of free nucleotide and a base nucleotide of a template DNA strand.

11 Claims, 9 Drawing Sheets

DNA SEQUENCING VIA DIRECT ELECTRICAL DETECTION WITH FREE SINGLE NUCLEOTIDE PAIRING WITH POLYMERASE

CROSS-REFERENCE

This application claims priority to U.S. provisional application No. 62/889,331 filed Aug. 20, 2019 and titled "DNA Sequencing Using Free Single Nucleotide Pairing with Direct Electrical Detection of Polymerase During Semiconservative Replication" the entire disclosure of which is incorporated herein by reference for all purposes.

BACKGROUND

Despite considerable efforts, current DNA sequencing methods face limitations in sequence read length, sensitivity, run time, and cost. To address these issues, various methods have been proposed that would allow individual DNA strands to be read directly. Among these, nanopore and nanochannel-based approaches have been proposed. However, many challenges exist related to fabricating a channel and/or pore opening that is sufficiently small to limit passage to a single DNA strand.

Other designs are needed.

SUMMARY

This disclosure is directed to DNA sequencing and devices therefor, particularly, to DNA sequencing and devices using free single nucleotides pairings with direct electrical detection of polymerase.

This disclosure provides, in one particular implementation, a DNA sequencing device having a first conductor electrically insulated from a second conductor, a voltage source and an amplifier, electrically connected in series with the first conductor and the second conductor, a DNA polymerase attached to the first conductor and to the second conductor with matching biotinylated tag molecules, and an electric current monitor.

In another particular implementation, this disclosure provides a method of DNA sequencing. The method includes providing a direct electrical detection of polymerase device, the device having a first conductor electrically insulated from a second conductor, a voltage source and an amplifier, electrically connected in series with the first conductor and the second conductor, and a DNA polymerase attached to the first conductor and to the second conductor, the conductors, voltage source, and amplifier forming a circuit. The method includes introducing a template DNA strand to the polymerase for transcription, applying a bias voltage to the circuit and measuring a current signal at an output of the amplifier, introducing free first nucleotides to the polymerase and monitoring the current signal for an increase, responsive to an increase in the current signal, detecting a match of a first nucleotide with a leading nucleotide of the template DNA strand or responsive to no increase in the current signal, determining no match of the first nucleotide with the leading nucleotide of the template DNA strand. After determining a match or no match, removing the free first nucleotides from the polymerase and introducing free second nucleotides different from the free first nucleotides to the polymerase and again monitoring the current signal for the increase.

This disclosure provides another particular implementation of a method of DNA sequencing using a device having a first conductor electrically insulated from a second conductor, a voltage source and an amplifier, electrically connected in series with the first conductor and the second conductor, and a DNA polymerase attached to the first conductor and to the second conductor via matched biotinylated tag molecules; the conductors, voltage source, and amplifier forming a circuit. The method includes introducing a template DNA strand to the polymerase, applying a bias voltage to the circuit and measuring a current signal at an output of the amplifier, the current signal having a baseline level, introducing a first type of free nucleotides to the polymerase and monitoring the current signal for an increase to a high level, the current signal increase provided by the polymerase during pairing and being non-discriminating on the type of free nucleotides being transcribed to the template DNA strand. Responsive to the current signal at the high level, determining a match of the first type of nucleotide with a leading nucleotide of the template DNA strand, or, responsive to the current signal at the baseline level, determining no match of the first type of nucleotide with the leading nucleotide of the template DNA strand.

The DNA sequencing device may be a microfluidic device, on a lab-on-a-chip platform with a physically or non-physically bounded fluid path, or may be on an electrode-gridded lab-on-a-chip. A microfluidic or lab-on-a-chip device provides a high level of parallelization.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. These and various other features and advantages will be apparent from a reading of the following detailed description.

BRIEF DESCRIPTION OF THE DRAWING

The described technology is best understood from the following Detailed Description describing various implementations read in connection with the accompanying drawing.

DETAILED DESCRIPTION

Figure 1:
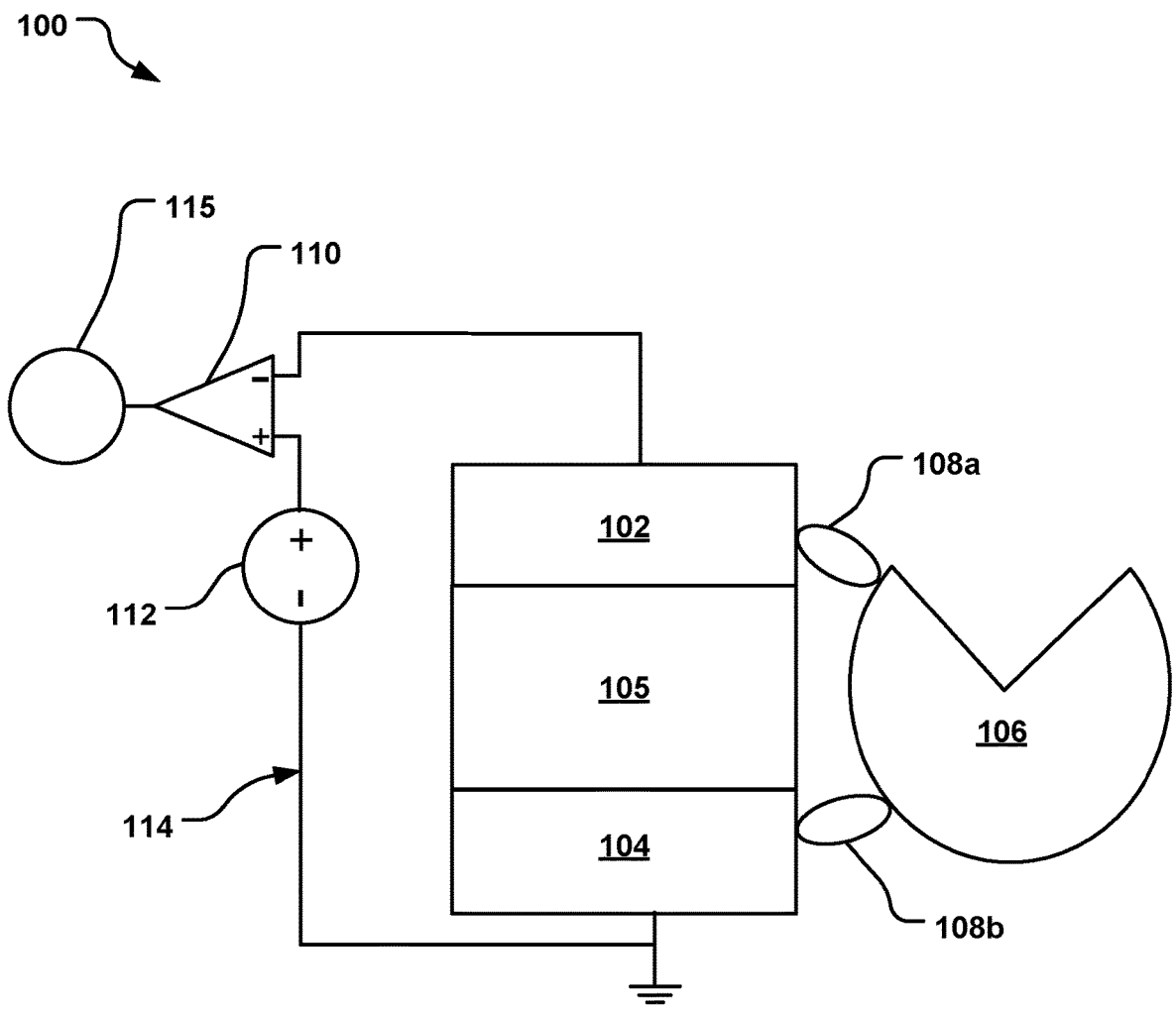
FIG. 1 is a schematic diagram of an example DNA sequencing device.

Current DNA sequencing methods face limitations in sequence read length, sensitivity, run time, and cost. As indicated above, this disclosure is directed to DNA sequencing and devices therefor that address these limitations. This disclosure provides DNA sequencing methods and devices that utilize free single nucleotide pairings with direct electrical detection of polymerase base pairing process.

DNA sequencing using direct electrical detection of protein/polymerase (DEMP) transcription has drawn attention as a method to sequence DNA directly using the unique electrical signature of the polymerase as it pairs a complementary nucleotide to a base nucleotide of a template DNA strand (single strand DNA) to form a double strand DNA. However, attempts to distinguish electrical signatures for the different nucleotide pairing event can be extremely difficult to resolve due to small differences in signal levels in the presence of noise and the stochastic nature of the pairing events.

The present disclosure is directed to DNA sequencing using direct electrical detection of a free single nucleotide pairing with polymerase. The present disclosure is also directed to DNA sequencing devices that perform such DNA sequencing.

The DNA sequencing device of this disclosure includes a first conductor and a second conductor, insulated from each other, and a voltage source and amplifier coupled in series with the conductors. A polymerase is operably attached to the conductors.

In use, the polymerase provides a conduction path between the two conductors, which gives rise to a baseline electrical signal. A template DNA strand introduced to the system is captured by the polymerase and is primed for transcription. The captured template strand modifies the overall conductance of the polymerase; the measured current level of this configuration is defined as the baseline signal level, "Io." When free, single nucleotides (e.g., A, C, T, G) are introduced to the polymerase, the appropriate complementary nucleotide will be paired to the template strand, one at a time. The electrical signal is non-discriminating to the particular nucleotide; that is each free nucleotide, whether A, C, T, G, will result in a change in the electrical signal from the baseline "To" value when transcribed.

The process requires that only one type of nucleotide is introduced at any given time and the signal monitored for any deviation from the baseline "Io." If a change in this non-discriminating electrical signal occurs, it is then known that the single base nucleotide of the template being paired is the complementary letter of the nucleotide that was introduced. If no signal change is observed, then the free nucleotide is washed away and a next nucleotide type is introduced and the process repeated for all letters of the nucleotide. Eventually, one of the free nucleotides will generate a signal indicating a matching pair event. This process is repeated for all bases in the template. In such a manner, the nucleotides of the template DNA strand are identified.

The polymerase may be attached to the first and second conductors with any biocompatible, at least semi-electrically conductive material, such as matching biotinylated tag molecules that link the conductors to the polymerase.

The device may be configured to monitor the electrical signal passing through the polymerase to determine when transcription occurs. Transcription will occur only if the free nucleotide is complementary to the base nucleotide of the template being paired by the polymerase. Upon transcription, a spike in electrical signal is observed, and thus the identity of the base nucleotide is known.

Each type of nucleotide (e.g., A, C, T, G) is introduced sequentially, one type at a time, with a wash or purification cycle between the introduction of each different nucleotide, to ensure that all previous nucleotides are removed and only the one type of (desired) nucleotide is present at the DNA polymerase with each introduction.

If transcription occurs (e.g., binding of a free nucleotide to the single strand DNA or template DNA strand via the polymerase), the electrical signal from the polymerase increases (e.g., to a high state), often with a series of spikes, and then reduces (e.g., to a low or original or baseline "Io" level) once pairing is complete. This indicates that there was a match of the free nucleotide to a base nucleotide that was ready for transcription, and the base nucleotide can be identified because it is the complementary nucleotide to the introduced nucleotide. If no increase in electrical signal is observed, they the free nucleotide may not match the base nucleotide.

A full template DNA sequence can be determined by monitoring the polymerase electrical signal response to the repeated cycles of free nucleotide introduction and wash cycles, until the template strand is fully transcribed. A full nucleotide cycle means the one-time introduction of all nucleotides, with a wash cycle between each.

The DNA sequencing method of this disclosure utilizes direct electrical detection as the polymerase pairs a free complementary nucleotide to a nucleotide of a template DNA strand to form a double strand DNA. The electrical signal (or, current signal) given by the polymerase during pairing is used as a marker to indicate that transcription is occurring. With this method, it is not necessary to identify from the electrical signal which nucleotides are being paired by the signal, but just that pairing is occurring. The base letter in the template strand is identified by the controlled introduction of a known nucleotide and by monitoring the signal for a pairing event.

When a single type of nucleotide (that is, one of A, C, T, G) is introduced to the polymerase, the electrical signal passing through the polymerase can be monitored to see if the specific nucleotide will be transcribed by the polymerase to the template DNA strand.

Each type of nucleotide is introduced, sequentially, with a cleansing or wash cycle between the introductions of different types; the wash cycle clears all free nucleotides before the introduction of the next nucleotide, to ensure that only the nucleotide being introduced is available for transcription with the base nucleotide of the template strand.

When transcription occurs, the electrical signal goes to a high state, with a series of spikes, and then returns to a low baseline "To" level when the pairing is complete; thus, this indicates that a match of the free nucleotide occurred with the base nucleotide of the template strand. The polymerase then moves the template strand through, by one base, in preparation to pair the next base in the template strand. However, if no signal increase is observed, that indicates that the free nucleotide was not a match to the base, and no transcription occurred.

Repeatedly introducing free nucleotides, one type at a time, during monitoring of the electrical signal, will eventually reconstruct the full single strand and hence provide the strand sequence by identifying which free nucleotide type gave a pairing signal when introduced.

In the following description, reference is made to the accompanying drawing that forms a part hereof and in which is shown by way of illustration at least one specific implementation. The following description provides additional specific implementations. It is to be understood that other implementations are contemplated and may be made without departing from the scope or spirit of the present disclosure.

The following detailed description, therefore, is not to be taken in a limiting sense. While the present disclosure is not so limited, an appreciation of various aspects of the disclosure will be gained through a discussion of the examples, including the figures, provided below. In some instances, a reference numeral may have an associated sub-label consisting of a lower-case letter to denote one of multiple similar components. When reference is made to a reference numeral without specification of a sub-label, the reference is intended to refer to all such multiple similar components.

Seen in FIG. 1, a sequencing device 100 is shown. The device 100 has a first conductor 102 and a second conductor 104, the two conductors 102, 104 being insulated from each other by an insulator 105, which in this implementation is a layer superimposed between the conductors 102, 104. The conductors 102, 104 may be any suitable material, such as platinum, gold, palladium, etc.

A DNA polymerase 106 is electrically connected to the first conductor 102 and to the second conductor 104. In this implementation, the polymerase 106 is connected to the conductors 103, 104 via a first attachment molecule 108a and a second attachment molecule 108b, respectively. The attachment molecules 108 can be any suitable, at least semi-electrically conductive molecules; the attachment molecule 108a may be the same or different than the attachment molecule 108b. In FIG. 1, the attachment molecules 108 are each biotinylated molecules, e.g., matching biotinylated tag molecules.

The conductors 102, 104 are electrically connected, in series, to a transimpedance amplifier 110 and a voltage source 112, forming an electrical circuit 114. A current monitor 115 (e.g., meter) is operably connected to the circuit to provide a qualitative or quantitative reading of the electrical current through the circuit 114.

Figure 2:
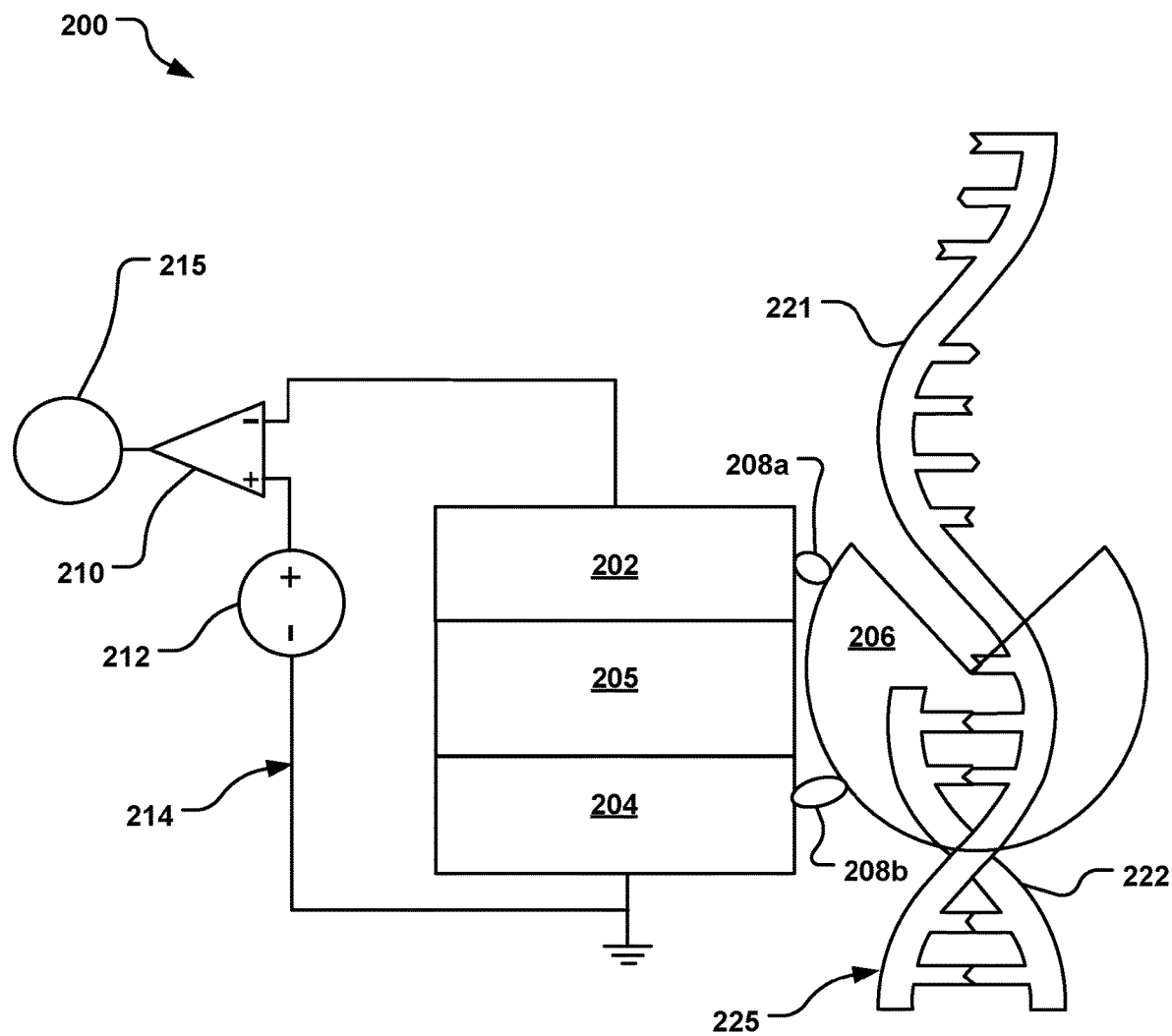
FIG. 2 is a schematic diagram of the DNA sequencing device of FIG. 1 with a template DNA strand being matched to its complementary base pair by the polymerase to form a double strand DNA.

FIG. 2 illustrates a sequencing device in use, building a complimentary DNA strand with the DNA polymerase from a single template DNA strand.

Seen in FIG. 2, a sequencing device 200 has a first conductor 202 and a second conductor 204, the two conductors 202, 204 insulated from each other by an insulator 205. A DNA polymerase 206 is electrically connected to the first conductor 202 and to the second conductor 204 via a first matching biotinylated tag molecule 208a and a second matching biotinylated tag molecule 208b. The conductors 202, 204 are electrically connected, in series, to a transimpedance amplifier 210 and a voltage source 212 forming an electrical circuit 214; current from the transimpedance amplifier 210 can be measured by a voltage measurement device or a current monitor 215.

A single strand, template DNA strand 221 is introduced to the polymerase 206. The polymerase 206 builds the complementary strand 222, forming a two strand DNA 225.

As the polymerase 206 builds the complementary strand 222, a bias voltage is provided (e.g., the voltage source 212 is turned on) and a signal current is measured at the output of the transimpedance amplifier 210 via the monitor 215.

Figure 3:
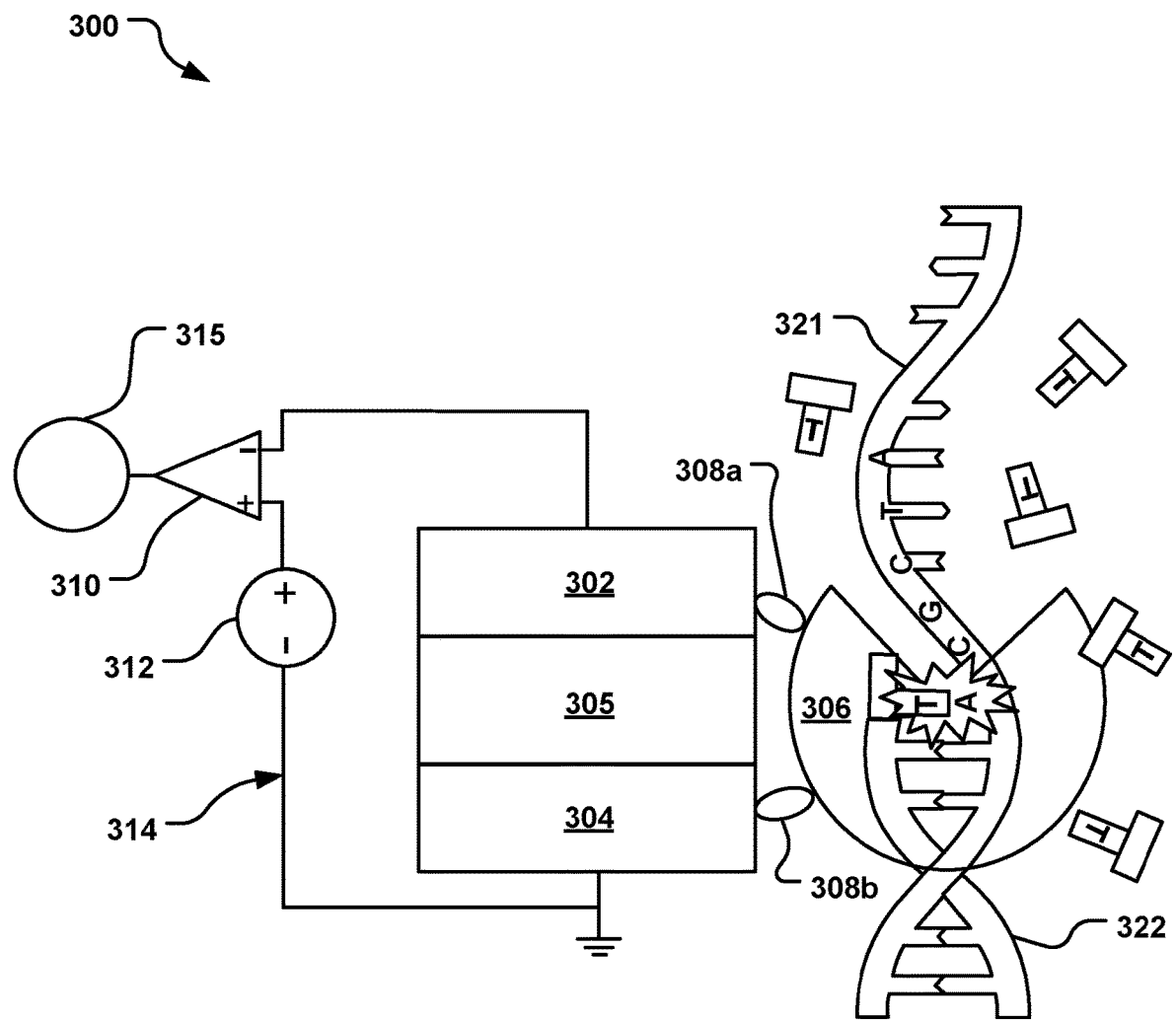
FIG. 3 is a schematic diagram of the DNA sequencing device of FIG. 1 with a first free nucleotide and a monitored signal current.

FIG. 3 illustrates the following step for a sequencing device in use, building a complimentary DNA strand with the DNA polymerase from a single strand, template DNA strand using free individual nucleotides, all of one type.

In FIG. 3, a sequencing device 300 has a first conductor 302 and a second conductor 304 insulated from each other by an insulator 305. A DNA polymerase 306 is electrically connected to the first conductor 302 and to the second conductor 304 via a first matching biotinylated tag molecule 308a and a second matching biotinylated tag molecule 308b. The conductors 302, 304 are electrically connected, in series, to a transimpedance amplifier 310 and a voltage source 312 forming an electrical circuit 314; current from the transimpedance amplifier 310 can be measured by a current monitor 315.

A single strand, template DNA strand 321 is introduced to the polymerase 306, which attempts to build the complementary strand 322 from free nucleotides T which are introduced to the device 300 in a solution or mixture. It is noted that the T nucleotide is the only nucleotide introduced at this time.

As the polymerase 206 builds the complementary strand 222, a bias voltage is provided (e.g., the voltage source 212 is turned on) and a signal current is measured at the output of the transimpedance amplifier 210 via the monitor 215.

If the T nucleotide is a complementary match to the first letter in the template strand 321 that is ready for transcription, then the current signal will go high, indicating that the T nucleotide was a match to the base (would have to be an A nucleotide). In this case, the first nucleotide in the template strand 321 is an A nucleotide, and the T nucleotide is the complementary based to the A nucleotide, therefore, the T nucleotide combines with the A nucleotide and results in a current increase or spike above the baseline "Io" level. The current spike reduces back to the baseline level when the transcription of the T nucleotide is complete and the template strand 321 is ratcheted to the next single base position. If the T nucleotide were not a match to the base, the current signal remains at its baseline "Io" value.

Figure 4:
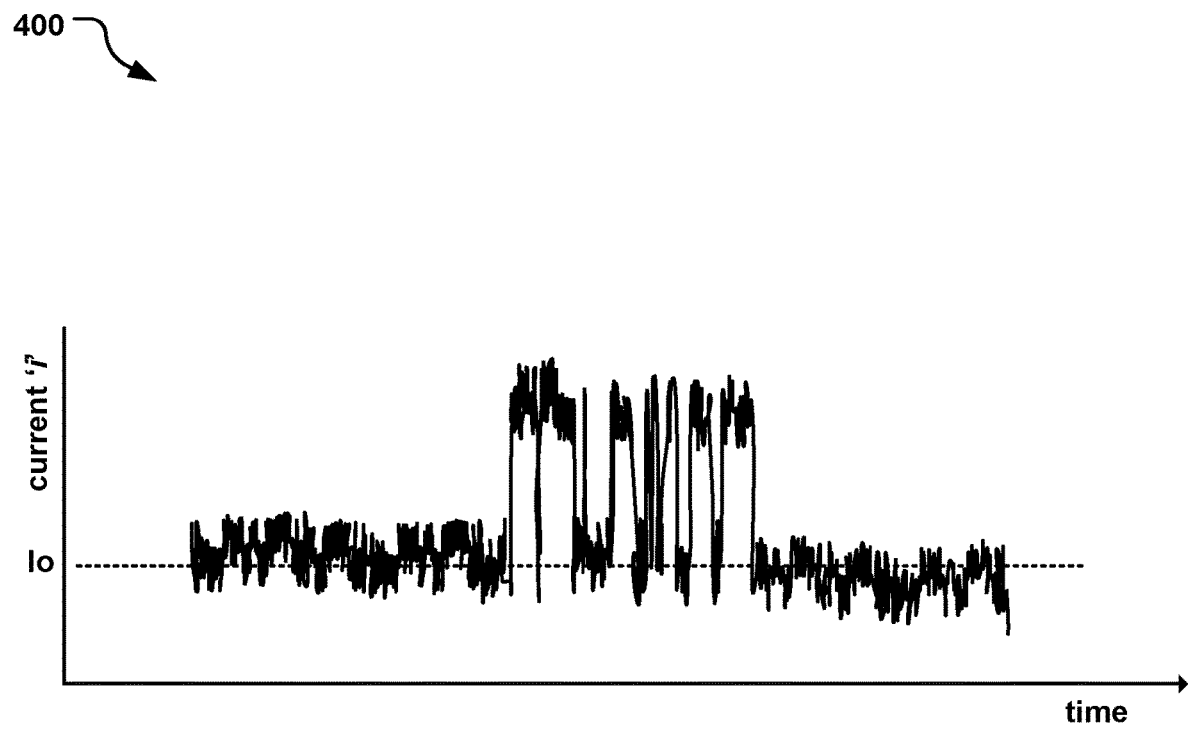
FIG. 4 is a graphical representation of current signal over time for nucleotide pairings.

A graph 400 in FIG. 4 illustrates an example current spike that occurs during the transcription. As seen in FIG. 4, the current has a baseline or low current "Io", which spikes or increases during transcription, and then returns to the baseline level. Although each type of nucleotide may produce a spike or increase of different magnitude, the method described herein relies on whether or not a spike or increase occurs, regardless of the magnitude, other than the spike or increase being a discernible and noteworthy increase over the baseline level. As seen in FIG. 4, the baseline or low level is not constant, but varies over time. The spike or increase should be at least 1.5× greater than a standard deviation of the baseline, in some implementations at least 2× greater than the standard deviation of the baseline.

The transcription spike or increase typically has a duration of hundreds of nanoseconds to tens of microseconds. The particular duration depends on numerous factors, including the specific DNA polymerase, the specific attachment molecule, the material of the conductors, etc.

Figure 5:
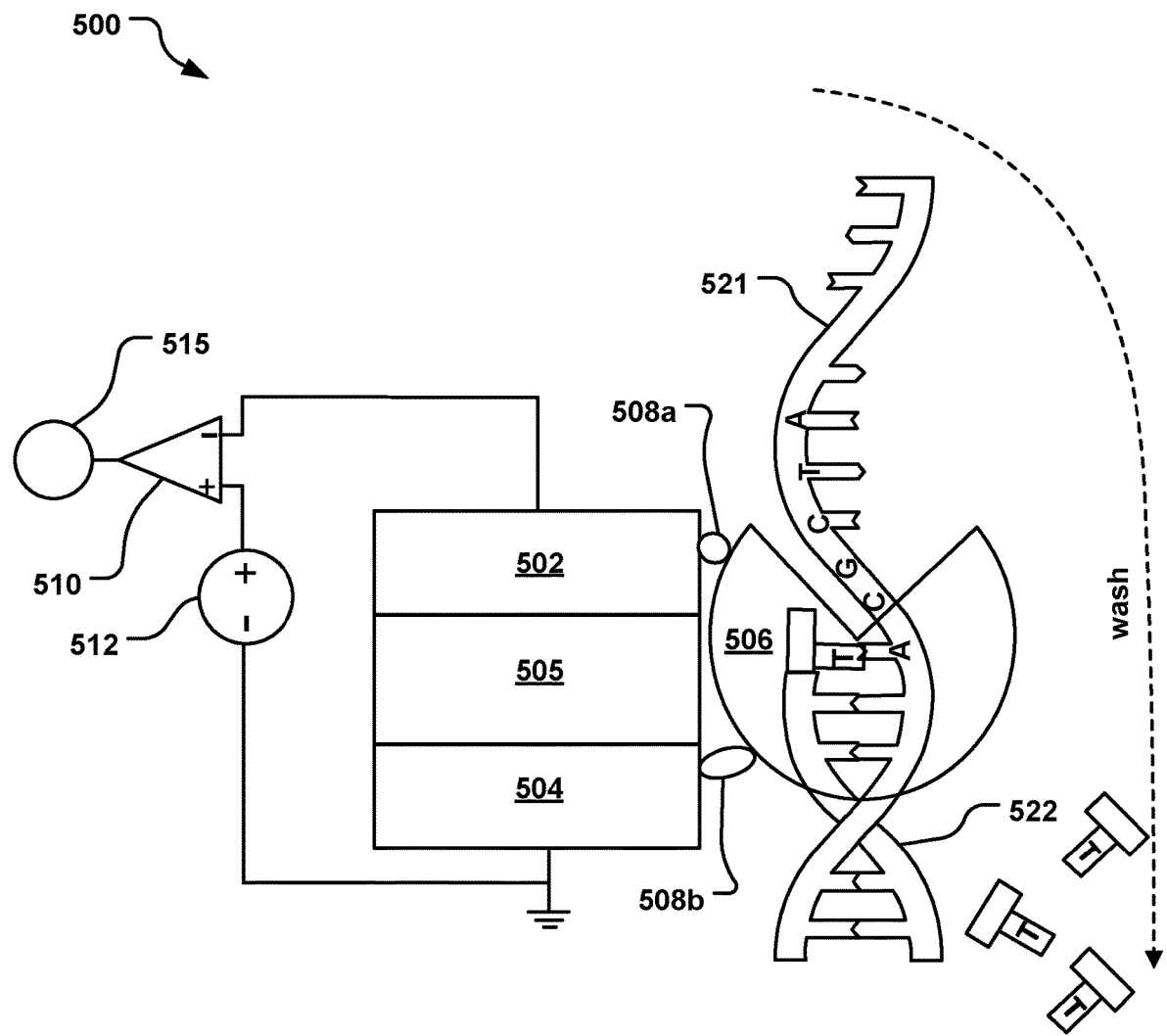
FIG. 5 is a schematic diagram of the DNA sequencing device of FIG. 1 showing free nucleotides washed away in a wash cycle.

FIG. 5 illustrates a step subsequent to FIG. 3. In FIG. 5, a sequencing device 500 has a first conductor 502 and a second conductor 504 insulated from each other by an insulator 505. A DNA polymerase 506 is electrically connected to the first conductor 502 and to the second conductor 504 via a first matching biotinylated tag molecule 508a and a second matching biotinylated tag molecule 508b. The conductors 502, 504 are electrically connected, in series, to a transimpedance amplifier 510 and a voltage source 512 forming an electrical circuit 514; current from the transimpedance amplifier 510 can be measured by a current monitor 515. The T nucleotide is seen incorporated into the complementary strand 522, paired with an A nucleotide of the template strand 521. After the incorporation of the T nucleotide to its complementary base A nucleotide, the template strand 521 is ratcheted down by one base position in preparation for the next transcription event.

The device 500 undergoes a wash cycle to remove all nucleotides T (and any other free nucleotides that may be present, e.g., from previous cycles) in preparation for the introduction of the next nucleotide. Such a wash cycle can be introduced after each nucleotide flow or before the next nucleotide flow.

Figure 6:
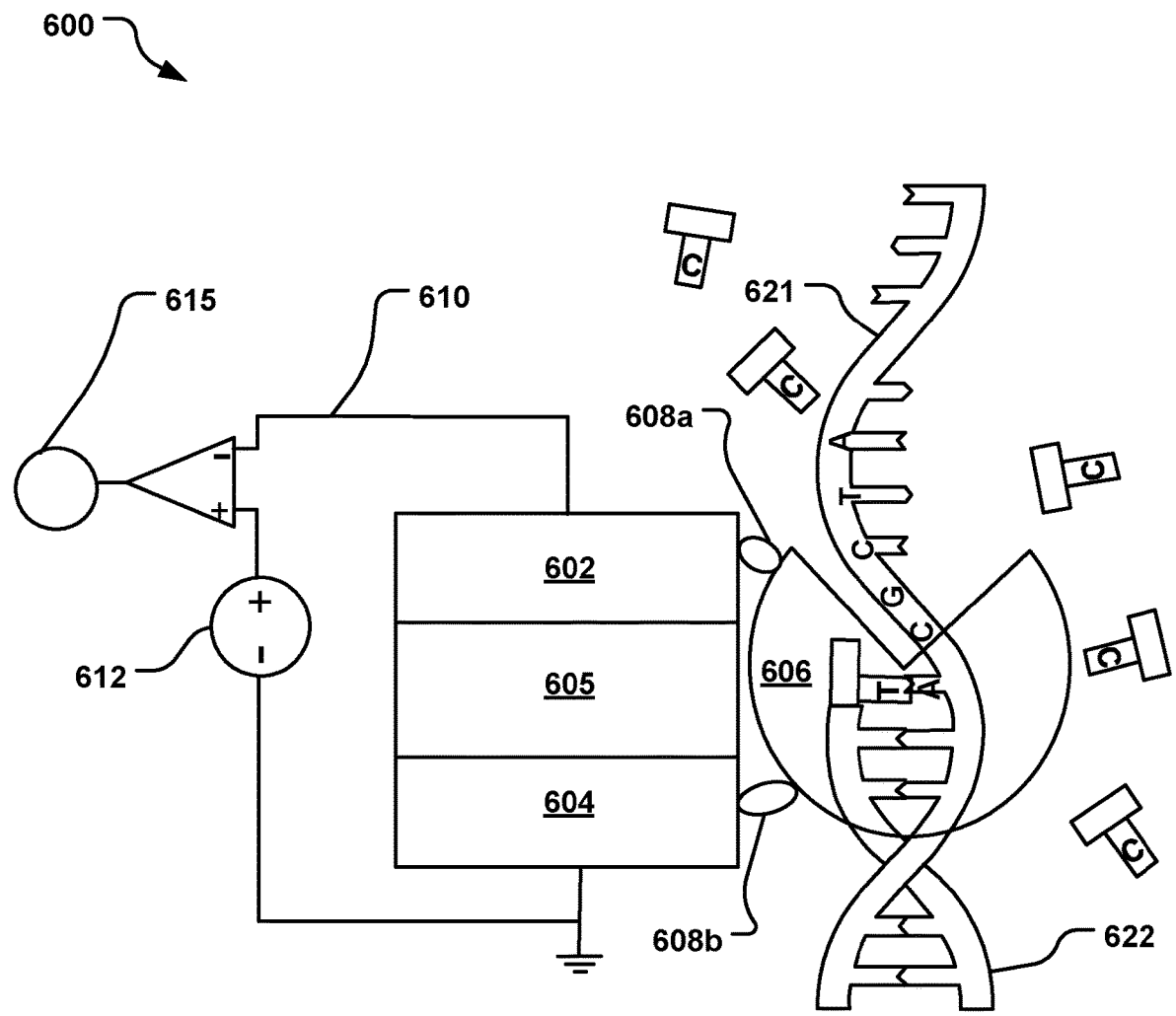
FIG. 6 is a schematic diagram of the DNA sequencing device of FIG. 1 with a second free nucleotide and a monitored signal current.

FIG. 6 illustrates a step subsequent to FIG. 5. In FIG. 6, a sequencing device 600 has a first conductor 602 and a second conductor 604 insulated from each other by an insulator 605. A DNA polymerase 606 is electrically connected to the first conductor 602 and to the second conductor 604 via a first matching biotinylated tag molecule 608a and a second matching biotinylated tag molecule 608b. The conductors 602, 604 are electrically connected, in series, to a transimpedance amplifier 610 and a voltage source 612 forming an electrical circuit 614; current from the transimpedance amplifier 610 can be measured by a current monitor 615.

The single strand, template DNA strand 621 is at the polymerase 606, which here attempts to build the complementary strand 622 from free C nucleotides present in or proximate to the device 600. As before, as the polymerase 606 builds the complementary strand 622, a bias voltage is provided (e.g., the voltage source 612 is turned on) and a signal current is measured at the output of the transimpedance amplifier 610 via the monitor 615.

If the C nucleotide is a complementary match to the first letter in the template strand 621 that is ready for transcription, then the current signal will go high, indicating that the C nucleotide is a match to the base (would have to be a G nucleotide). In this case, the first nucleotide in the template strand 621 is an C nucleotide, and the free C nucleotide does not combine with the C nucleotide of the strand 621, thus, there is no match and the current does not waver. If the free C nucleotide were a match to the base nucleotide, the current signal would spike.

A (different) third and subsequent nucleotides may subsequently be introduced to the polymerase after a cleansing or wash cycle before each introduction to remove all free nucleotides already present. With each nucleotide introduced, the signal current (I) is monitored, looking for spikes from the baseline ("Io") that would indicate transcription and thus identity of the base nucleotides.

The repeated cycle of adding each type of nucleotide, sequentially with a wash cycle in between each nucleotide, is done until the single strand, template transcription is complete. In such a manner, the single strand is sequenced one base nucleotide at a time.

Figure 7:
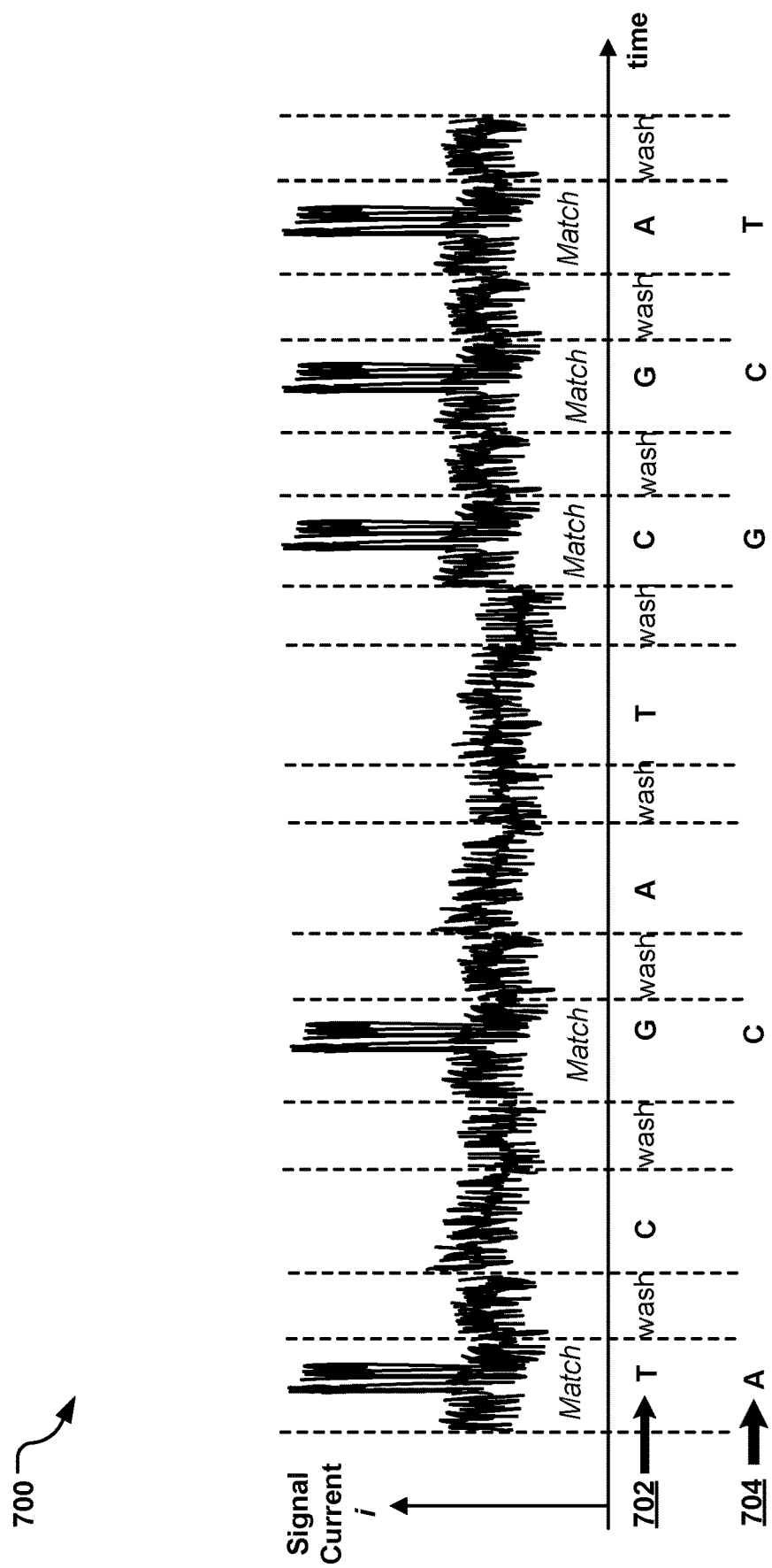
FIG. 7 is a graphical representation of current signal over time of the polymerase current flow signal during repeated wash and single nucleotide introduction cycles.

Turning to FIG. 7, a graph 700 shows an example of a sequencing process for the following template sequence: A C G C T. The free nucleotide introduction order is T C G A, with a wash cycle between each nucleotide introduction. The introduction/wash cycles continue until the entire template is fully transcribed. Although the free nucleotides could be introduced in any order, or randomly, a repeating order is easy to maintain and monitor.

The order of introduction of the free nucleotides is not important, other than not repeating a nucleotide type until the base nucleotide is transcribed. For example, one would not introduce the nucleotides in the order A G T A C if none of the first A, the G nor the T transcribed the base. However, the order A G T A could be used if one of the first A, the G or the T did transcribe the base nucleotide.

In some occurrences, a nucleotide in the template strand may repeat (i.e., at least two of the same nucleotides in sequence). This would be detected by multiple pulses with a return to the baseline level between pulse events. This type of signal would indicate multiple repeat bases being paired until the repeat sequence ends in the template strand.

Returning to FIG. 7, the graph 700 shows that the signal current (i), in this particular example, has a fairly level baseline or low state and has five occurrences at a high state (e.g., spiked). An active signal in the high state (e.g., spike) indicates that the introduced free nucleotide was paired with the base nucleotide by the DNA polymerase.

Although each type of nucleotide may produce a spike or increase of different magnitude, the method of this disclosure relies on whether or not a spike or increase occurs, regardless of the magnitude, other than the spike or increase being discernible increase over the baseline. The spike or increase should be at least 1.5× or at least 2× greater than a standard deviation of the baseline.

Therefore, the reconstruction of the single strand template sequence is done by noting the template base in the time series of the matching free nucleotide. In the example of FIG. 7, the first free T nucleotide (in line 702) was a match to a base A nucleotide (indicated in line 704), the next free C nucleotide (in line 702) was not a match, the next free G nucleotide (in line 702) was a match to a base C nucleotide (indicated in line 704), the next free A nucleotide (in line 702) was not a match, the next free T nucleotide (in line 702) was not a match, the next free C nucleotide (in line 702) was a match to a base G nucleotide (indicated in line 704), the next free G nucleotide (in line 702) was match to a base C nucleotide (indicated in line 704), and the next free A nucleotide (in line 702) was a match to a base T nucleotide (indicated in line 704). Thus, the transcribed sequence is T G C G T and the sequenced base is A C G C T.

In such a manner, the devices of this disclosure provide a method of DNA sequencing. Thus, another aspect of this disclosure relates to a method of DNA sequencing that includes providing a direct electrical detection of a polymerase device having an electrical circuit coupled thereto, providing a template DNA strand to the polymerase, applying a voltage bias and measuring a current, and flowing free first nucleotides across the polymerase while monitoring the current. Responsive to monitoring a current spike, detecting a match of the first nucleotide with the leading nucleotide of the template DNA strand. Responsive to monitoring no current spike or increase, not detecting a match of the first nucleotide with the leading nucleotide of the template DNA strand. Subsequently to either detection, conducting a cleansing or wash cycle to remove the free first nucleotides.

The method also includes, responsive to not detecting a match of the first nucleotide with the leading nucleotide of the template DNA strand, flowing free second nucleotides different than the first nucleotide across the polymerase while monitoring the current. Responsive to monitoring a current spike, detecting a match of the second nucleotide with the leading nucleotide of the template DNA strand. Responsive to monitoring no current spike or increase, not detecting a match of the second nucleotide with the leading nucleotide of the template DNA strand. Subsequently to either detection, conducting a cleansing or wash cycle to remove the free second nucleotides.

The method also includes, responsive to not detecting a match of the second nucleotide with the leading nucleotide of the template DNA strand, flowing free third nucleotides different than the first nucleotide and different than the second nucleotide across the polymerase while monitoring the current. Responsive to monitoring a current spike, detecting a match of the third nucleotide with the leading nucleotide of the template DNA strand. Responsive to monitoring no current spike or increase, not detecting a match of the third nucleotide with the leading nucleotide of the template DNA strand. Subsequently to either detection, conducting a cleansing or wash cycle to remove the free third nucleotides.

The method still further includes, responsive to not detecting a match of the third nucleotide with the leading nucleotide of the template DNA strand, flowing free fourth nucleotides different than the first nucleotide, different than the second nucleotide, and different than the third nucleotide across the polymerase while monitoring the current. Responsive to monitoring a current spike, detecting a match of the fourth nucleotide with the leading nucleotide of the template DNA strand. Responsive to monitoring no current spike or increase, not detecting a match of the fourth nucleotide with the leading nucleotide of the template DNA strand. Subsequently to either detection, conducting a cleansing or wash cycle to remove the free fourth nucleotides.

The method may additional include, responsive to detecting a match with any of the first, second, third or fourth nucleotide with the leading nucleotide, flowing any one of free first nucleotides, free second nucleotides, free third nucleotides, or free fourth nucleotides across the polymerase while monitoring the current.

The method may include repeating any or all of the flowing nucleotide steps, sequentially, until the complete transcription of the template strand is complete.

The electrical circuit may have first and second insulated conductors or electrodes, an amplifier and a voltage source, with the polymerase electrically coupled to the two conductors or electrodes. The insulated conductors may be a first conductor and a second conductor, with an insulating layer therebetween.

Figure 8:
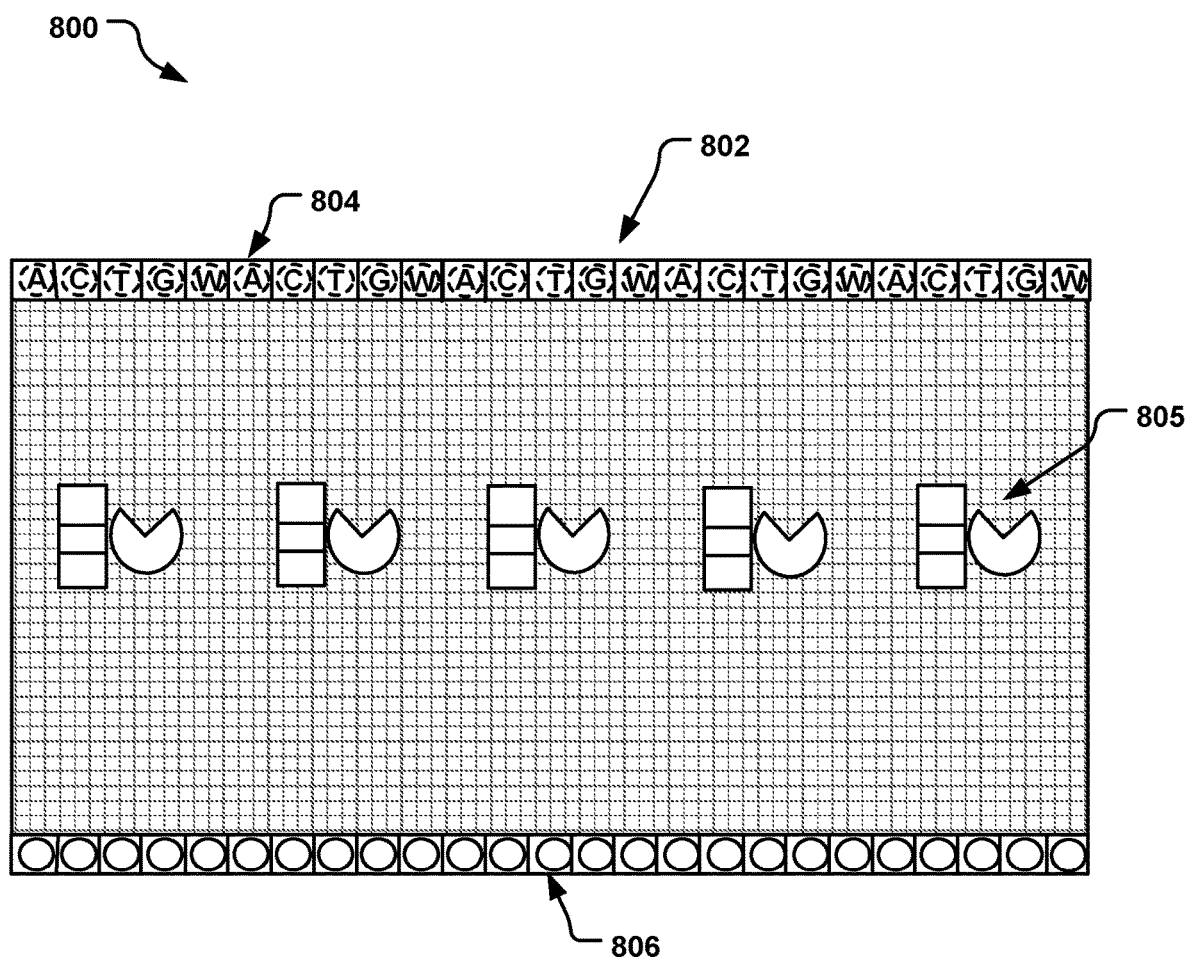
FIG. 8 is a schematic diagram of a microfluidic lab-on-a-chip DNA sequencing device.
Figure 9:
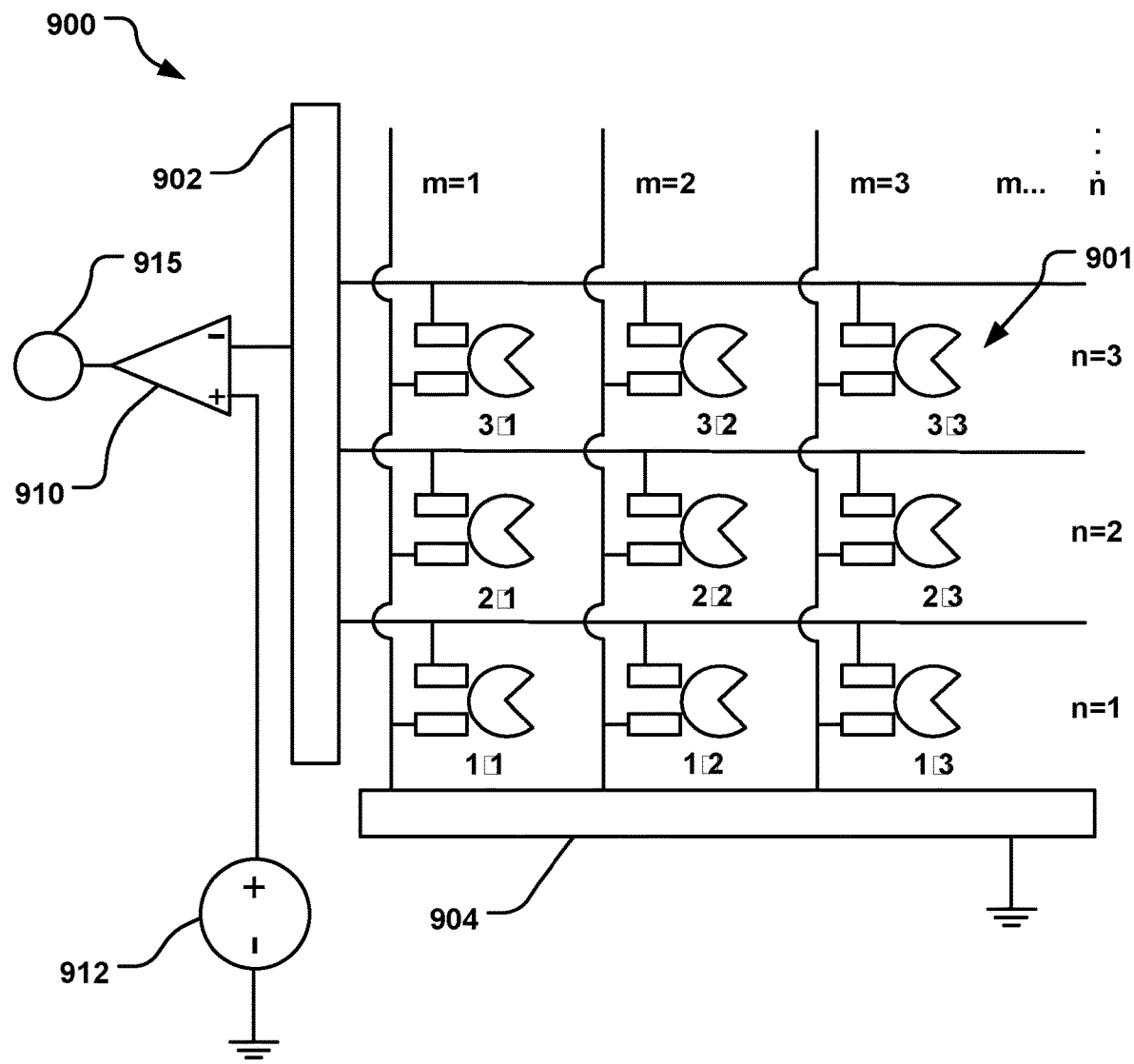
FIG. 9 is a schematic diagram of a system having multiple DNA sequencing devices in parallel.

The previously described and illustrated devices and methods utilize a single DNA sequencing device having a single polymerase and conductor pair and the cyclical single nucleotide type introduction and wash process. The sequential nature of introduction of one free nucleotide at a time, with a wash cycle between each introduction, implies that the sequencing process might be very slow. To overcome the slow nature of this sequencing process, a high degree of parallelization can be incorporated into the sequencing devices and methods. FIGS. 8 and 9 provide two examples, both which can be implemented on a lab-on-a-chip microfluidic platform.

The DNA sequencing devices and systems can be provided as microfluidic or nanofluidic systems. One particular microfluidic system is a microfluidic lab-on-a-chip system. A microfluidic or lab-on-a-chip system for the DNA sequencing device allows a high degree of parallelization of multiple devices.

Lab-on-a-chip is a common term for an integrated circuit ("chip") on which one or several laboratory functions or chemical reactions are done. The chip can be no more than a few square centimeters. Labs-on-a-chip handle extremely small fluid volumes (e.g., measured as e.g., microliters, nanoliters, or pico-liters) and are often called microfluidic systems. In digital microfluidics, the lab-on-a-chip has a hydrophobic "chip platform" on which fluid droplets (e.g., liquid droplets) can be manipulated by precisely controlled voltage application.

The chip may be formed from two or more detachable parts: one part containing the electronics (e.g., voltage source, amplifier, current meter) and another part containing the polymerase and attachment molecules (e.g., biotinylated tag molecules). Such a construction would enable the reuse of expensive electronic pieces while allowing the fluidic area to be disposable. The platform may have a cover plate covering the fluidic area.

By utilizing the feature of surface tension of the fluid on the platform, the free nucleotides and the wash liquid (e.g., water) can be precisely moved across the platform by voltage applied to the platform, e.g., in a grid. Alternately, the platform working surface has an insulating layer (e.g., silicon, silicon dioxide, etc.) over the working surface and at least one channel through the insulating layer to the working surface. The channel provides a physical conduit for the free nucleotides and the wash liquid (e.g., water).

FIG. 8 shows a microfluidic system 800, having a platform working surface 802, also referred to as a lab-on-a-chip, having a plurality of wells 804 on a first side and a plurality of wells 806 on the opposite side. The wells 804 has present therein free nucleotides (labeled as A, C, T, G) and liquid for a wash cycle. Present on the working surface 802 are five DNA sequencing devices 805, the figure showing two conductors, an insulating layer, and a DNA polymerase; each device 805 has one set of wells 804, one each of A nucleotide, C nucleotide, T, nucleotide, G nucleotide and wash liquid. Electrically connected to the conductors (but not shown in FIG. 8) are a voltage source, an amplifier, and a current monitor for each device 805. Also not shown in FIG. 8 are template DNA strands.

The working surface 802 has numerous cells each configured to independently receive a voltage. In this implementation, the cells of the platform 802 control the movement of the free nucleotides and the wash liquid thereon by the voltage applied to the cells. Using known techniques (e.g., voltage differential on the platform), the free nucleotides and the wash liquid are moved on (across) the platform to the device 805 where transcription occurs if the free nucleotide is complementary to a base nucleotide of the template DNA strand.

In another implementation, the platform working surface 802 has an insulating layer (e.g., silicon, silicon dioxide, etc.) over the working surface and a plurality of channels present through the insulating layer to the working surface. The channels provide a physical boundary for the free nucleotides, the wash liquid, and the template DNA strand, the channels directing the fluids across the working surface 802. Either voltage from the cells in the working surface or any numbers of pumps or microfluidic pressurizers can be used to move the free nucleotides, the wash liquid, and the template DNA strand.

FIG. 9 shows another DNA sequencing device having a high degree of parallelization of multiple devices. FIG. 9 shows a microfluidic system 900 having an "n×m" array of sequencing devices 901 on a microfluidic cell; e.g., device 1,1 where n=1 and m=1, device 2,1 where n=2 and m=1, etc. In this system 900, the cycles of the free nucleotide and the wash are introduced to all sequencing devices 901 simultaneously.

As with the previously described sequencing devices, each of the devices 901 has a two conductors (electrodes) insulated from each other and a DNA polymerase attached to the conductors with biotin. Each of the first conductors (electrodes) is connected to a first multiplex conductor 902 and each of the second conductors (electrodes) is connected to a second multiplex conductor 904. The multiplex conductors 902, 904 are electrically connected, in series, to a transimpedance amplifier 910, a voltage source 912 and a current monitor 915. In use, a distinct template DNA strand is incorporated with each DNA polymerase for each device

901; in some implementations, a particular template strand may be incorporated in two different devices 901, e.g., for control purposes.

As before, one type of free nucleotide is introduced sequentially to the system 900 and each device 901 with a wash in between each introduction.

Although all the devices 901 are connected in parallel to the same current monitor 915, each sequencing device 901 is monitored individually by employing a cross point connection to the multiplexers 902, 904, which sample the current of every sequencing device 901 of the system 900. A controller (not shown in FIG. 9) controls the switching from one device 901 to the next and samples the current monitor 915 for each n,m device during each cycle of nucleotide exposure. In such a manner, the nucleotide introduction and wash cycle are used by all devices 901 of the system 900 to transcribe the multiple unique template strands simultaneously. With such a system 900, having massive parallelization, the total sequencing throughput is significantly increased.

The above specification and examples provide a complete description of the structure and use of exemplary implementations of the invention. The above description provides specific implementations. It is to be understood that other implementations are contemplated and may be made without departing from the scope or spirit of the present disclosure. The above detailed description, therefore, is not to be taken in a limiting sense. While the present disclosure is not so limited, an appreciation of various aspects of the disclosure will be gained through a discussion of the examples provided. Furthermore, structural features of the different implementations may be combined in yet another implementation without departing from the disclosure or the recited claims.

Unless otherwise indicated, all numbers expressing feature sizes, amounts, and physical properties are to be understood as being modified by the term "about," whether or not the term "about" is immediately present. Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass implementations having plural referents, unless the content clearly dictates otherwise. As used in this specification and the appended claims, the term "or" is generally employed in its sense including "and/or" unless the content clearly dictates otherwise.

Spatially related terms, including but not limited to, "bottom," "lower", "top", "upper", "beneath", "below", "above", "on top", "on," etc., if used herein, are utilized for ease of description to describe spatial relationships of an element(s) to another. Such spatially related terms encompass different orientations of the device in addition to the particular orientations depicted in the figures and described herein. For example, if a structure depicted in the figures is turned over or flipped over, portions previously described as below or beneath other elements would then be above or over those other elements.

Since many implementations of the invention can be made without departing from the spirit and scope of the invention, the invention resides in the claims hereinafter appended.

What is claimed is:

1. A method for DNA sequencing comprising:
    providing a direct-electrical-detection-of-polymerase device having a first conductor electrically insulated from a second conductor, a voltage source and an amplifier electrically connected in series with the first conductor and the second conductor, and a DNA polymerase attached to the first conductor and to the second conductor, the conductors, voltage source, and amplifier forming a circuit;
    introducing a template DNA strand to the polymerase for transcription;
    applying a bias voltage to the circuit and measuring a current signal at an output of the amplifier;
    introducing a first type of free nucleotides to the polymerase and monitoring the current signal for an increase;
    responsive to an increase in the current signal, detecting a pairing of a first type of free nucleotide with a leading nucleotide of the template DNA strand, and responsive to no increase in the current signal, determining no pairing of the first type of free nucleotide with the leading nucleotide of the template DNA strand;
    after determining a pairing or no pairing, removing the first type of free nucleotides from the polymerase; and
    introducing a second type of free nucleotides different from the first type of free nucleotides to the polymerase and monitoring the current signal for the increase.

2. The method of claim 1, further comprising, after introducing the second type of free nucleotides:
    responsive to an increase in the current signal, detecting a pairing of a second type of free nucleotide with a leading nucleotide of the template DNA strand, and responsive to no increase in the current signal, determining no pairing of the second type of free nucleotide with the leading nucleotide of the template DNA strand; and
    after determining a pairing or no pairing, removing the second type of free nucleotides from the polymerase.

3. The method of claim 2, further comprising, after removing the second type of free nucleotides:
    introducing a third type of free nucleotides different from the first type of free nucleotides and the second type of free nucleotides to the polymerase and monitoring the current signal for the increase;
    responsive to an increase in the current signal, detecting a pairing of a third type of free nucleotide with a leading nucleotide of the template DNA strand, and responsive to no increase in the current signal, determining no pairing of the third type of free nucleotide with the leading nucleotide of the template DNA strand; and
    after determining a pairing or no pairing, removing the third type of free nucleotides from the polymerase.

4. The method of claim 3, further comprising, after removing the third type of free nucleotides:
    introducing a fourth type of free nucleotides different from the first type of free nucleotides, the second type of free nucleotides and the third type of free nucleotides to the polymerase and monitoring the current signal for the increase;
    responsive to an increase in the current signal, detecting a pairing of a fourth type of free nucleotide with a leading nucleotide of the template DNA strand, and responsive to no increase in the current signal, determining no pairing of the fourth type of free nucleotide with the leading nucleotide of the template DNA strand; and
    after determining a pairing or no pairing, removing the fourth type of free nucleotides from the polymerase.

5. The method of claim 4, further comprising repeating the introduction of each type of free nucleotide sequentially with a removal of the nucleotides in between introduction of a different type of free nucleotide until complete transcription of the template DNA strand is complete.

6. A method for DNA sequencing comprising:
providing a device having a first conductor electrically insulated from a second conductor, a voltage source and an amplifier, electrically connected in series with the first conductor and the second conductor, and a DNA polymerase attached to the first conductor and to the second conductor via matched biotinylated tag molecules; the conductors, voltage source, and amplifier forming a circuit;
introducing a template DNA strand to the polymerase;
applying a bias voltage to the circuit and measuring a current signal at an output of the amplifier, the current signal having a baseline level;
introducing a first type of free nucleotides to the polymerase and monitoring the current signal for an increase to a high level, the current signal increase provided by the polymerase during pairing and being non-discriminating on the type of free nucleotide being transcribed to the template DNA strand; and
responsive to the current signal at the high level, determining a pairing of the first type of nucleotide with a leading nucleotide of the template DNA strand, and responsive to the current signal at the baseline level, determining no pairing of the first type of nucleotide with the leading nucleotide of the template DNA strand.

7. The method of claim 6, further comprising, after determining a pairing or no pairing, removing the first type of free nucleotides.

8. The method of claim 7, further comprising, after removing the first type of free nucleotides, introducing a second type of free nucleotides different from the first type of nucleotides to the polymerase and monitoring the current signal for the high level.

9. The method of claim 8, further comprising, after introducing the second type of free nucleotides:
responsive to the current signal at the high level, determining a pairing of the second type of nucleotide with a leading nucleotide of the template DNA strand, and responsive to the current signal at the low baseline level, determining no pairing of the second type of nucleotide with the leading nucleotide of the template DNA strand; and
after determining a pairing or no pairing, removing the second type of free nucleotides from the polymerase.

10. The method of claim 9, further comprising, after removing the second type of free nucleotides:
introducing a third type of free nucleotides different from the first type of free nucleotides and the second type of free nucleotides to the polymerase and monitoring the current signal for the increase;
responsive to an increase in the current signal, detecting a pairing of a third type of nucleotide with a leading nucleotide of the template DNA strand, and responsive to no increase in the current signal, determining no pairing of the third type of nucleotide with the leading nucleotide of the template DNA strand; and
after determining a pairing or no pairing, removing the third type of free nucleotides from the polymerase.

11. The method of claim 10, further comprising, after removing the third type of free nucleotides:
introducing a fourth type of free nucleotides different from the first type of free nucleotides, the second type of free nucleotides and the third type of free nucleotides to the polymerase and monitoring the current signal for the increase;
responsive to an increase in the current signal, detecting a pairing of a fourth type of nucleotide with a leading nucleotide of the template DNA strand, and responsive to no increase in the current signal, determining no pairing of the fourth type of nucleotide with the leading nucleotide of the template DNA strand; and
after determining a pairing or no pairing, removing the fourth type of free nucleotides from the polymerase.

* * * * *